United States Patent
Okihara

(10) Patent No.: US 10,507,280 B2
(45) Date of Patent: *Dec. 17, 2019

(54) MEDICAL INSTRUMENT HOUSING CONTAINER

(71) Applicant: TERUMO KABUSHIKI KAISHA, Tokyo (JP)

(72) Inventor: Hitoshi Okihara, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/115,477

(22) Filed: Aug. 28, 2018

(65) Prior Publication Data

US 2019/0001050 A1   Jan. 3, 2019

Related U.S. Application Data

(63) Continuation of application No. 14/660,099, filed on Mar. 17, 2015, now Pat. No. 10,086,131, which is a (Continued)

(51) Int. Cl.
*A61M 5/00* (2006.01)
*B65D 77/20* (2006.01)
(Continued)

(52) U.S. Cl.
CPC ............ *A61M 5/002* (2013.01); *A61B 50/20* (2016.02); *A61B 50/22* (2016.02); *A61B 50/30* (2016.02);
(Continued)

(58) Field of Classification Search
CPC ..... A61M 5/002; A61M 5/008; B65D 79/005; B65D 77/2024; A61B 50/30
(Continued)

(56) References Cited

U.S. PATENT DOCUMENTS

| 4,466,552 A | 8/1984 | Butterworth et al. |
| 5,830,547 A | 11/1998 | MacKenzie et al. |

(Continued)

FOREIGN PATENT DOCUMENTS

| CN | 1234421 C | 1/2006 |
| DE | 10301386 A1 | 11/2003 |

(Continued)

OTHER PUBLICATIONS

European Patent Office, "Communication with Extended European Search Report," issued in connection with European Patent Application No. 13870832.6, dated Jul. 14, 2016.

(Continued)

*Primary Examiner* — Steven A. Reynolds
(74) *Attorney, Agent, or Firm* — Foley & Lardner LLP

(57) ABSTRACT

A medical instrument housing container includes a container body including a substantially rectangular base, a peripheral wall having a lower end that is contiguous to a perimeter of the base and that extends upward, and a peripheral edge member that comprises a plurality of peripheral edges, that is contiguous to an upper end of the peripheral wall, and that extends outwardly, wherein the substantially rectangular base, the peripheral wall, and the peripheral edge member are molded from resin, and the container body has an opening surrounded by the peripheral edge member; a plurality of medical instruments held in the container body; and a protection film that is adhered or heat-sealed to the peripheral edge member for covering and sealing the opening. At least a portion of the peripheral edge member is curved inwardly. The protection film covers the opening in a flexed condition.

18 Claims, 5 Drawing Sheets

Related U.S. Application Data continuation of application No. PCT/JP2013/050189, filed on Jan. 9, 2013.

(51) Int. Cl.

| | | |
|---|---|---|
| *B65D 79/00* | (2006.01) | |
| *A61B 50/22* | (2016.01) | |
| *A61B 50/20* | (2016.01) | |
| *A61B 50/30* | (2016.01) | |
| *A61B 50/33* | (2016.01) | |
| *A61L 2/07* | (2006.01) | |
| *A61B 50/00* | (2016.01) | |

(52) U.S. Cl.
CPC .......... *A61B 50/33* (2016.02); *B65D 77/2024* (2013.01); *B65D 79/005* (2013.01); *A61B 2050/0065* (2016.02); *A61B 2050/3006* (2016.02); *A61L 2/07* (2013.01); *A61M 5/008* (2013.01)

(58) Field of Classification Search
USPC ........................................ 206/366, 364, 365
See application file for complete search history.

(56) References Cited

U.S. PATENT DOCUMENTS

| | | | |
|---|---|---|---|
| 6,629,602 | B1 | 10/2003 | Heyman |
| 7,303,073 | B2 | 12/2007 | Raynal-Olive et al. |
| 8,100,263 | B2 | 1/2012 | Vanderbush et al. |
| 8,679,404 | B2 | 3/2014 | Liburd et al. |
| 10,086,131 | B2 * | 10/2018 | Okihara ............. B65D 77/2024 |
| 2005/0103666 | A1 | 5/2005 | Grimard et al. |
| 2010/0270197 | A1 | 10/2010 | Porret et al. |
| 2012/0118777 | A1 | 5/2012 | Kakiuchi et al. |

FOREIGN PATENT DOCUMENTS

| | | |
|---|---|---|
| JP | 3012092 U | 6/1995 |
| JP | 2004-513707 A | 5/2004 |
| JP | 2005-500080 A | 1/2005 |
| JP | 2012-071046 A | 4/2012 |
| JP | 2012-100927 A | 5/2012 |
| JP | 2012-140183 A | 7/2012 |
| WO | WO-02/40065 A1 | 5/2002 |

OTHER PUBLICATIONS

International Searching Authority, "International Search Report," issued in connection with International Patent Application No. PCT/JP2013/050189, dated Apr. 23, 2013.

International Searching Authority, "Written Opinion," issued in connection with International Patent Application No. PCT/JP2013/050189, dated Apr. 23, 2013.

Japanese Patent Office, "Notification of Reasons for Refusal," issued in connection with Japanese Patent Application No. 2014-556248, dated Mar. 3, 2016.

Japanese Patent Office, "Notification of Reasons for Refusal," issued in connection with Japanese Patent Application No. 2014-556248, dated Oct. 21, 2016.

The State Intellectual Property Office of People's Republic of China, "The First Office Action," issued in connection with Chinese Patent Application No. 201380046142.5, dated Dec. 30, 2015.

\* cited by examiner

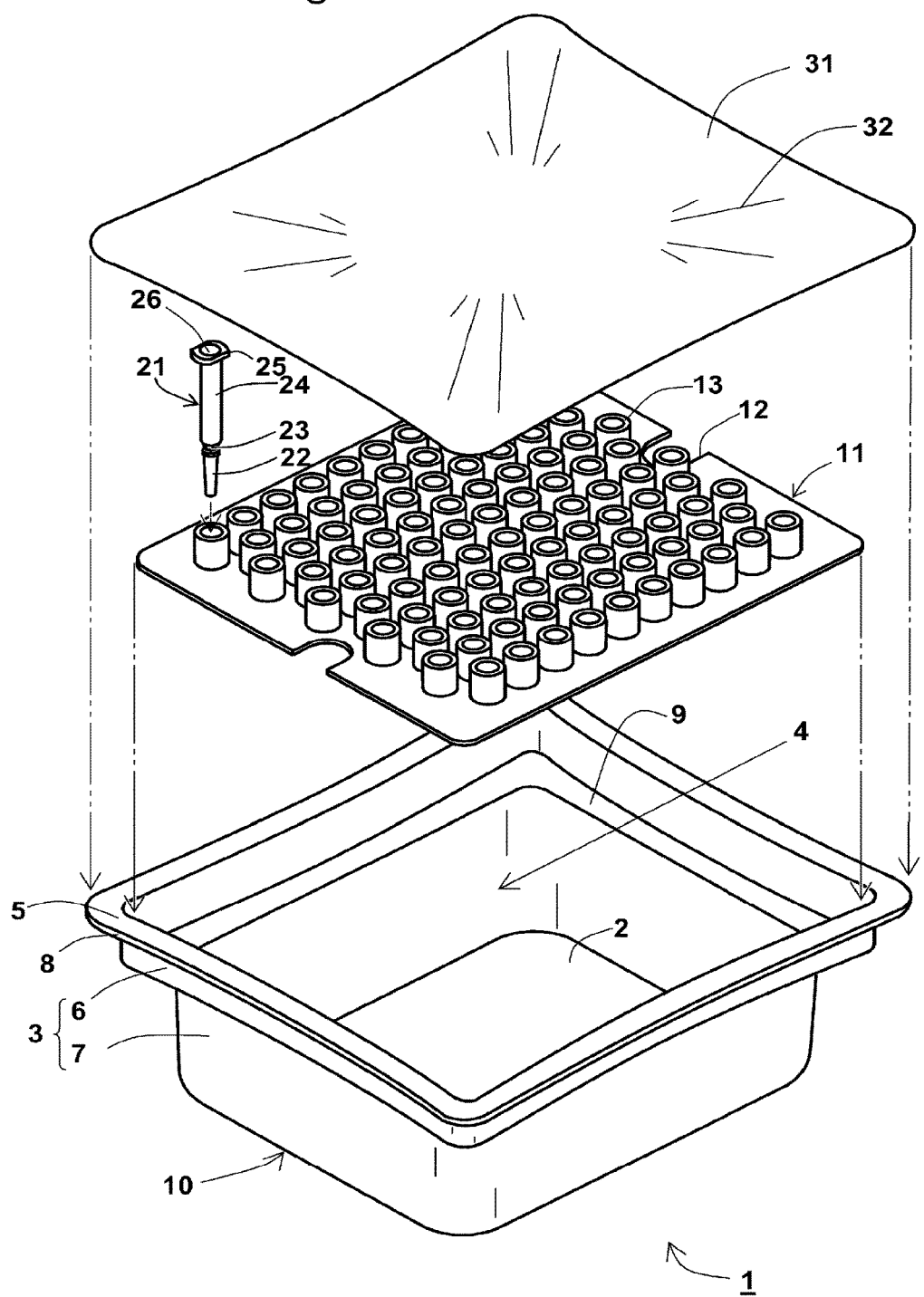

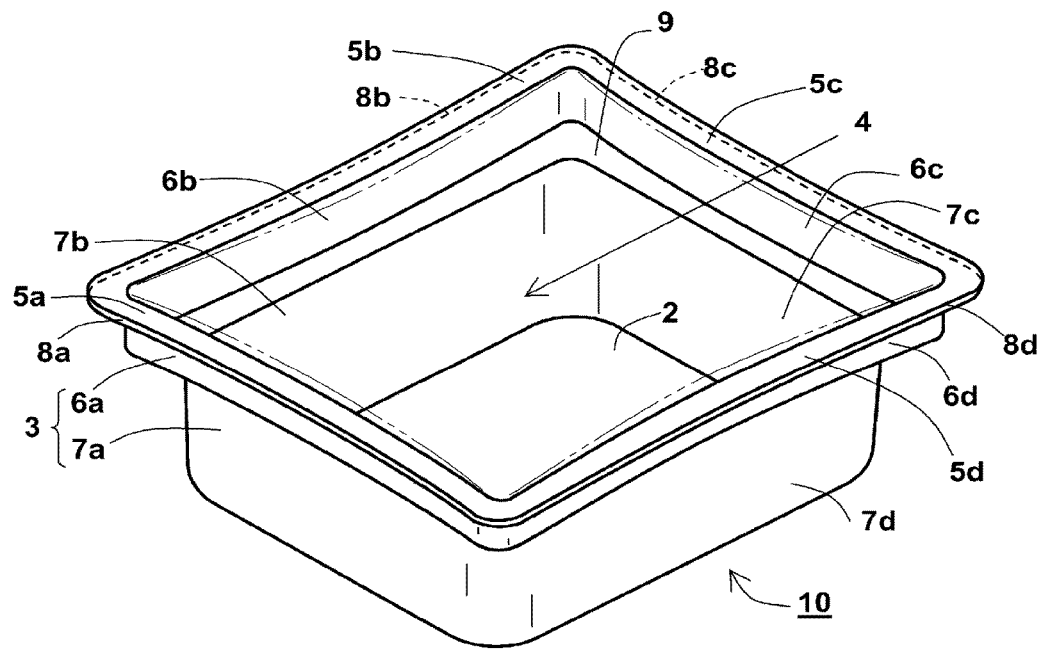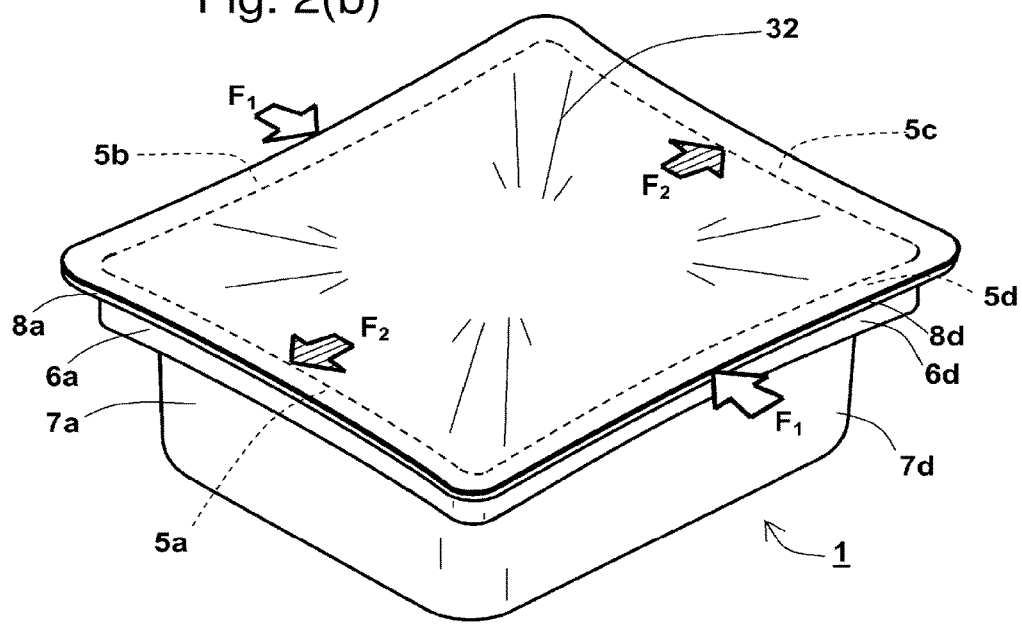

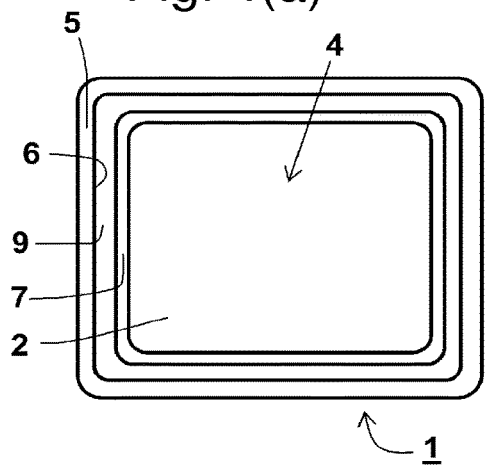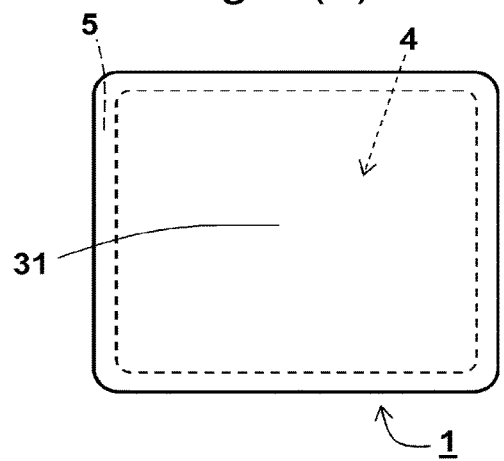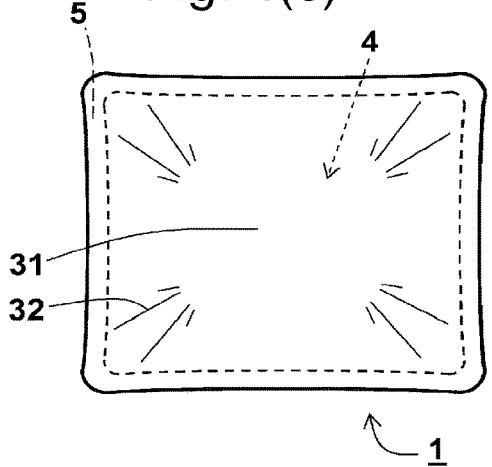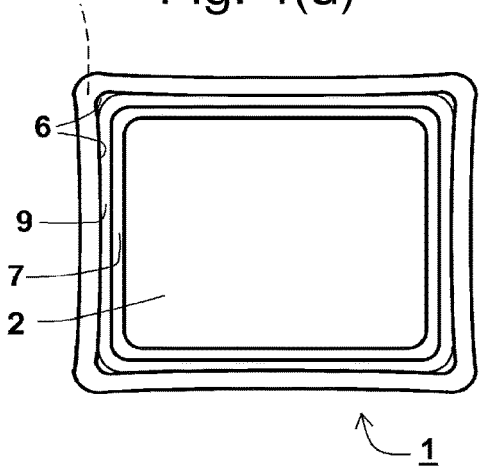

MEDICAL INSTRUMENT HOUSING CONTAINER

CROSS-REFERENCE TO RELATED APPLICATIONS

This application is a continuation of U.S. patent application Ser. No. 14/660,099, filed on Mar. 17, 2015, which is a continuation application filed under 35 U.S.C. 111(a) claiming the benefit under 35 U.S.C. §§ 120 and 365(c) of PCT International Application No. PCT/JP2013/050189, filed on Jan. 9, 2013, the entire contents of which are hereby incorporated by reference in their entireties.

BACKGROUND

Technical Field

The present disclosure relates to a medical instrument housing container that holds medical instruments such as medical devices and pharmaceutical products and is sterilized.

Background Art

Medical instruments including medical devices such as prefilled syringes with syringe barrels prefilled with a drug and prefillable syringes therefor, syringes, needles, blood collection bags, blood collection instruments, and catheters, and pharmaceutical products such as vial bottles are contained and sterilized in medical instrument containers, aseptically packaged, and opened for use in medical facilities.

Taking prefilled syringes as an example, first, in a manufacturing factory of prefillable syringes, prefillable syringes are contained in substantially rectangular parallelepipedic, disposable containers that are made of resin and suitable for transport and storage. The containers are then sealed by a protection film via a layer of adhesive, sterilized, and transported to a factory where the syringe barrels are to be filled with a drug. In the latter factory, the prefillable syringes are taken out of the containers, filled with the drug, and then a plunger is inserted into the syringes to make prefilled syringes. The prefilled syringes thus produced are enclosed in sterile packaging bags and transported to users such as doctors.

As an example of such a housing container used for transporting medical instruments that require sterilization, JP 2004-513707 W describes a multipurpose package including a plastic tub and a cover fixed to the tub so as to seal the tub with an impervious sealing zone. The multipurpose package can be used to accommodate sterile products or products intended to be sterilized.

For such a housing container, it is necessary that the sealed and sterile conditions inside the container holding medical instruments are maintained all the way through distribution and storage. However, the housing container, which is typically a substantially rectangular parallelepipedic casing, is subject to substantial profile change as a result of application of stresses which it cannot withstand, in the form of vibration, impacts due to a fall or a collision, external pressure, and the like during packing, transport, or storage. Especially, the edge of an opening covered with a protection film at the top of the container is most likely to deform due to concentration thereto of stresses such as vibration, impacts, external pressure, or the like. Furthermore, as shown in FIG. 5(c), for example, due to the straightness of peripheral edges as individual sides of the substantially rectangular opening, when an external stress $F_1$ is applied to a paired, parallel, and opposing peripheral edges 55a, 55c of a housing container 50, peripheral edges 55b, 55d therebetween are pushed outwardly. As is shown by the two-dot dashed lines, when the peripheral edges 55b, 55d are deformed outwardly, a protection film 31 can be forcefully pulled outwardly and eventually be detached as it is unable to follow the deformation. Thus, even if the protection film 31 has securely sealed the opening, the protection film 31 can be detached as it is unable to follow the deformation of the peripheral edges 55b, 55d of the housing container 50, and consequently, the container is unable to maintain the sealed condition thereof.

There is a desire for a medical instrument housing container that can prevent detachment of a protection film due to stresses such as vibration, impacts, external pressure, and the like during packing, transport, or storage, so that the sealed and sterile conditions thereof are maintained.

SUMMARY OF INVENTION

One objective of certain embodiments of the present invention is to provide a medical instrument housing container that is capable of buffering deformation due to stresses such as vibration, impacts, external pressure, and the like and absorbing such stresses so as to prevent detachment of a protection film due to the stresses during packing, transport, or storage and that is further capable of preventing detachment of the protection film during sterilization so as to maintain the inside sealed and sterile conditions.

According to one embodiment, a medical instrument housing container includes a container body including: a substantially rectangular base, a peripheral wall having a lower end that is contiguous to a perimeter of the base and extending upward, and a peripheral edge member that comprises a plurality of peripheral edges, that is contiguous to an upper end of the peripheral wall, and that extends outwardly. The substantially rectangular base, the peripheral wall, and the peripheral edge member are molded from resin, and the container body has an opening surrounded by the peripheral edge member. The medical instrument housing container further includes one or more medical instruments held in the container body; and a protection film that is adhered or heat-sealed to the peripheral edge member for covering and sealing the opening. The medical instrument housing container is a medical instrument housing container that has been subjected to sterilization. At least a portion of the peripheral edge member is curved inwardly. The protection film covers the opening in a flexed condition.

In one aspect, at least two opposing peripheral edges of the peripheral edge member are curved inwardly.

In one aspect, the opening is substantially rectangular with a longer side having a length in a range of 225 to 245 mm and a shorter side having a length in a range of 190 to 210 mm. The peripheral wall has a thickness of 0.5 to 3 mm.

In one aspect, the peripheral wall has a ledge disposed around and protruding inward from an inner wall surface of the peripheral wall. The medical instrument housing container further includes a nest tray configured to hold the medical instrument, the nest tray being mounted on the ledge.

In one aspect, the peripheral wall is divided into an upper peripheral wall surface contiguous to an outer edge of the ledge and extending toward the peripheral edge member and a lower peripheral wall surface contiguous to an inner edge of the ledge and extending toward the base.

In one aspect, the one or more medical instruments comprise a plurality of syringe barrels intended to be filled with a drug, each having a cap at a distal end and a flange at a proximal end. A plurality of receiving cylinders configured to receive the plurality of syringe barrels is disposed such that the receiving cylinder extend through the nest tray, the receiving cylinders being organized in rows.

In one aspect, at least a portion of the peripheral edge member has an inward curvature in a range of 1 to 5 mm.

In one aspect, the protection film is a nonwoven sheet made of resin that is gas permeable and impervious to particulates.

In one aspect, the sterilization is autoclaving. As a result of the autoclaving, the peripheral edge member is curved inward and the protection film that has been adhered or heat-sealed to the peripheral edge member is flexed.

In one aspect, the peripheral edge member has a width in a range of 7 to 30 mm.

In one aspect, the ledge has a width in a range of 5 to 30 mm.

In one aspect, the opening is substantially rectangular with a longer side having a length in a range of 225 to 245 mm and a shorter side having a length in a range of 190 to 210 mm. The peripheral wall has a thickness of 0.5 to 3 mm.

In one aspect, the peripheral wall has a ledge disposed around and protruding inward from an inner wall surface of the peripheral wall. The medical instrument housing container further includes a nest tray configured to hold the medical instrument, the nest tray being mounted on the ledge.

In one aspect, the peripheral edge member comprises a first pair of two opposing peripheral edges curved inwardly and a second pair of two opposing peripheral edges curved inwardly.

A medical instrument housing container according to certain embodiments of the present invention is of a type in which a wall surface of a peripheral wall of a container body and a peripheral edge contiguous thereto are formed having a pre-shaped inward curve or a curve toward the inside of the container body. As a result of this, when stresses caused by external forces such as vibration, impacts, external pressure, and the like are applied to the medical instrument housing container, possible deformation thereof is oriented inwardly or toward the inside of the container body, and the protection film is instantaneously flexed to absorb the stresses, resulting in buffering of the deformation. Furthermore, even if outward deformation takes place, the original flection of the protection film allows the protection film to follow the deformation and thus prevent detachment of the protection film.

In one aspect, during sterilization, especially due to high temperature and high humidity from autoclaving, the wall surface of the peripheral wall of the container and the peripheral edge contiguous thereto are deformed only inwardly of the container along with shrinkage of the protection film. Thus detachment of the protection film is prevented.

Hence, in accordance with the medical instrument housing container, the sealed and sterile conditions within the container body are maintained so that the medical instruments contained are protected from contamination.

BRIEF DESCRIPTION OF DRAWINGS

FIG. 1 is an exploded perspective view of a medical instrument housing container according to an embodiment of the present invention.

FIG. 2(a) is a perspective view of a container body of the medical instrument housing container.

FIG. 2(b) is a perspective view of the medical instrument housing container

FIG. 4(a) is a plan view showing the medical instrument housing container in a state prior to both containing medical instruments and sterilization.

FIG. 4(b) is a plan view showing the medical instrument housing container in a state containing medical instruments and sealed by a protection film, prior to sterilization.

FIG. 4(c) is a plan view showing the medical instrument housing container in a state sealed by the protection film post autoclaving.

FIG. 4(d) is a plan view showing the medical instrument housing container in a state after sterilization and after removal of the protection film.

DETAILED DESCRIPTION

Detailed description of embodiments of the present invention will now be provided; however, these embodiments are not intended to limit the scope of the present invention.

Figure 3:
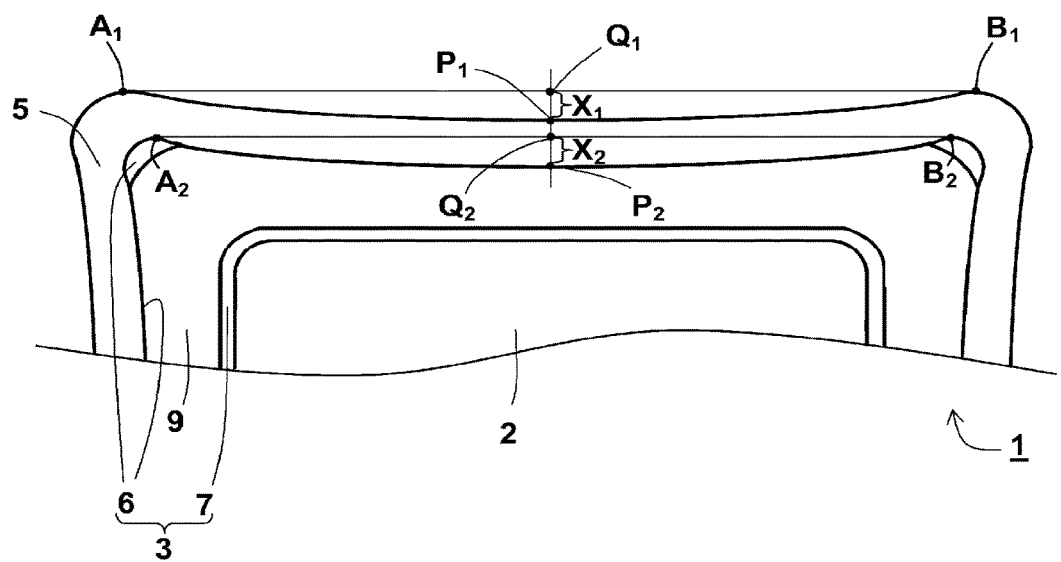
FIG. 3 is a schematic partially enlarged plan view of the container body of the medical instrument housing container.

Referring to FIGS. 1 to 3, an embodiment of a medical instrument housing container 1 of the present invention will now be described.

FIG. 1 is an exploded perspective view of the medical instrument housing container 1 holding medical instruments that are syringe barrels 21 intended to be filled with a drug. As is shown in FIG. 1, a medical instrument housing container 1 is a substantially rectangular parallelepipedic casing. In a container body 10 of the medical instrument housing container 1, a substantially square base 2 is contiguous with a peripheral wall 3 that is extended upward from and surrounding the base 2, and an opening 4 is defined as surrounded by an upper end of the peripheral wall 3. The container body 10 is tapered toward the base 2, which has a smaller area compared to the opening 4. A middle portion of the peripheral wall 3 is further tapered forming a ledge 9 that is disposed around and extends horizontally from an inner wall surface of the peripheral wall 3 toward the inside of the container body 10. Around the opening 4, a peripheral edge 5 formed as a flange having a uniform width extends contiguously and outwardly from the upper end of the peripheral wall 3. Medical instruments intended to be sterilized, such as medical devices and pharmaceutical products, are held in the container body surrounded by the base 2 and the peripheral wall 3. The base 2, the peripheral wall 3, the ledge 9, and the peripheral edge 5 are integrally made of thermoplastic resin.

On the ledge 9 of the medical instrument housing container 1, a nest member 11 is mounted so as to hold medical instruments. The nest member 11 has a substantially rectangular shape that is slightly smaller than the opening 4 of the medical instrument housing container 1 and is the right size to fit on the ledge 9. The nest tray 11 has a plurality of cylindrical receiving cylinders 13 therethrough, each individually having an open upper end and an open lower end. The cylindrical receiving cylinders 13 are spaced from one another in a plurality of rows. The nest tray 11 has two notches 12 sized so that a finger can be inserted therethrough to pick up the nest tray 11 to put it into or take it out of the medical instrument housing container 1.

The syringe barrel 21 has a cap 22 covering a nozzle 23, a syringe body 24, and a flange 25 around a proximal-end opening 26. The receiving cylinders 13 can removably and insertably receive a plurality of syringe barrels 21 therethrough. The syringe barrels 21 are individually inserted into each of the receiving cylinders 13. The receiving cylinders 13 lock the syringe barrels 21 by the flange 25 and suspend them.

The inside of the medical instrument housing container 1 is sealed by a protection film 31 that is gas permeable and impervious to particulates, e.g. a nonwoven sheet made of resin, adhered or heat-sealed to the peripheral edge 5 formed on the top face of the medical instrument housing container 1 contiguously to the opening 4 that is surrounded by the upper end of the peripheral wall 3.

FIG. 2(a) shows a perspective view of just the container body 10 of the medical instrument housing container 1, while FIG. 2(b) shows a perspective view of the medical instrument housing container 1. The container body 10 includes a pair of opposing peripheral edge side faces 8a, 8c and another pair of opposing peripheral edge side faces 8b, 8d of the peripheral edge 5 symmetrically curved inwardly or toward the inside of the container body 10 in an arc shape, respectively, as a result of the shrinkage of resin. Correspondingly, the peripheral edges 5a, 5b, 5c, 5d of the same width along four sides of the opening 4 are curved toward the inside of the container body in an arc shape. As a result of the curved peripheral edges 5a, 5b, 5c, 5d, the protection film 31 that is originally a flat sheet becomes flexed. It should be noted that the protection film 31 in this embodiment has wrinkles 32 caused by the flection.

The peripheral wall 3 that is a lateral side of the container body 10 includes an upper peripheral wall surface 6 connecting the peripheral edge 5 and the ledge 9, and a lower peripheral wall surface 7 connecting the ledge 9 and the base 2. Corresponding to the curves of the peripheral edges 5a, 5b, 5c, 5d, one pair of opposing upper peripheral wall surfaces 6a, 6c and another pair of opposing upper peripheral wall surfaces 6b, 6d of the peripheral wall 3 are symmetrically curved inwardly or toward the inside of the container body 10 in an arc shape, respectively. Because the opening 4 is subject to deformation by stresses, the peripheral edges 5a, 5b, 5c, 5d and the upper peripheral wall surfaces 6a, 6b, 6c, 6d can be curved by the shrinkage of resin. In contrast, the ledge 9 is horizontal and securely supported by the corners of adjacent lower peripheral wall surfaces 7a, 7b, 7c, 7d to be resistant to deformation; therefore, the lower peripheral wall surfaces 7a, 7b, 7c, 7d and the base 2 are hardly curved even with the shrinkage of resin.

When an external force is applied to the container body 10, the lower ends of all the upper peripheral wall surfaces 6a, 6b, 6c, 6d are supported by the ledge 9 and the upper ends of the same defining the deformable opening 4 are inwardly inclined, thus, as is shown by the two-dot dashed lines, the peripheral edges 5a, 5b, 5c, 5d together with the peripheral edge side faces 8a, 8b, 8c, 8d are further deformable in an arc-shaped curve. When an external force is applied to the medical instrument housing container 1 and results in application of a lateral stress $F_1$ to the peripheral edge side faces 8b, 8d as shown in FIG. 2(b), the peripheral edges 5b, 5d are further deformed in an arc-shaped curve. On the other hand, the paired peripheral edges 5a, 5c between the peripheral edges 5b, 5d are subjected to a stress $F_2$, whereby the upper ends of the upper peripheral wall surfaces 6a, 6c are outwardly inclined, outwardly moving the peripheral edges 5a, 5c together with the protection film 31. Here, in addition to the curves themselves absorbing stresses applied thereto, the protection film 31 over the opening 4 in a flexed condition (in this embodiment, with wrinkles 32) is capable of absorbing the outward stress $F_2$ by stretching the flection (in this embodiment, wrinkles 32) thereof. Further, deformation of the peripheral edges 5a, 5c can be buffered. Hence, even if these external forces are applied to the container body 10, the external forces hardly affect the protection film 31; therefore, the protection film 31 remains attached.

The curve in the medical instrument housing container 1 shown in FIGS. 2(a) and 2(b) is exaggeratedly shown in FIG. 3 as a schematic partially enlarged plan view. Shown in FIG. 3 is a curvature corresponding to the degree of a curve of one side of the peripheral edge 5 of the medical instrument housing container 1.

A curvature is determined from a distance between a straight line connecting two outermost vertexes, each of which residing near opposite ends of an arc-shaped side of the symmetrical peripheral edge 5, and an innermost vertex at about the center of the arc-shaped side of the peripheral edge 5. For example, when a virtual perpendicular line is drawn from a center $Q_1$ of a virtual straight line connecting outermost vertexes, namely, an originating point $A_1$ and a terminating point $B_1$ residing near opposite ends of an arc-shaped side of the peripheral edge 5 outer circumference, a distance between the center $Q_1$ and a cross-over point $P_1$ of the virtual perpendicular line and the peripheral edge 5 outer circumference (i.e., the innermost vertex of the peripheral edge 5 outer circumference) is a curvature $X_1$. Similarly, when a virtual perpendicular line is drawn from a center $Q_2$ of a virtual straight line connecting outermost vertexes, namely, an originating point $A_2$ and a terminating point $B_2$ residing near opposite ends of an arc-shaped side of the peripheral edge 5 inner circumference, a distance between the center $Q_2$ and a cross-over point $P_2$ of the virtual perpendicular line and the peripheral edge 5 inner circumference (i.e., the innermost vertex of the peripheral edge 5 inner circumference) is a curvature $X_2$. Because the peripheral edge 5 goes around with a uniform width, the curvatures $X_1$ and $X_2$ should present as substantially the same value.

The curvatures $X_1$ and $X_2$ are respectively 5 mm maximum, preferably from 1 to 5 mm, and more preferably from 23 mm. It follows that the peripheral edge side faces 8a, 8b, 8c, 8d of the peripheral edge 5 are curved by the values of the curvatures $X_1$ and $X_2$.

Curvatures of the upper peripheral wall surfaces 6a, 6b, 6c, 6d are smaller than the curvatures $X_1$ and $X_2$. Curvatures of the lower peripheral wall surfaces 7a, 7b, 7c, 7d and the base 2 are nearly zero.

The medical instrument housing container 1 is manufactured as will be described in the following with reference to FIGS. 4(a) to 4(d) showing the manufacturing process.

FIG. 4(a) is a plan view of the medical instrument housing container 1 in a state prior to both containing medical instruments and sterilization. First, as shown in FIG. 4(a), the medical instrument housing container 1 is molded into a shape wherein a substantially rectangular opening 4 composed of straight sides without twist or warpage, a planar peripheral edge 5 therearound with similarly straight sides, and a lower peripheral wall surface 7 connecting a ledge 9 on which a nest member 11 is mounted and a base 2 are planar without a curve or a bend, having flat side faces.

FIG. 4(*b*) is a plan view of the medical instrument housing container 1 after containing medical instruments (not shown) and sealed by a protection film 31, prior to sterilization. In the medical instrument housing container 1, a nest member 11 is placed with medical instruments, for example, a plurality of syringe barrels 21 being inserted into receiving cylinders 13. The nest member 11 is mounted on the ledge 9 (see FIG. 1). As shown in FIG. 4(*b*), the opening 4 is covered with the protection film 31 so as to cover the contained medical instruments, and the protection film 31 is adhered or heat-sealed to the peripheral edge 5, such that the inside of the medical instrument housing container 1 is sealed.

The medical instrument housing container 1, in the sealed state, is autoclaved in an autoclave sterilization chamber. In this autoclave step for sterilizing the medical instrument housing container 1 using a high temperature, high pressure saturated water vapor, the protection film 31 and the container body 10, being made of resin, shrink to some extent. Here, the corners jointing the upper peripheral wall surfaces 6a, 6b, 6c, 6d are gently bent so that they are rigid and hardly deformed. In contrast, due to the shrinkage of resin and due to the fact that the internal pressure of the sealed container body 10 is lower than that of the autoclave sterilization chamber, the peripheral edges 5a, 5b, 5c, 5d that have been adhered or heat-sealed to the protection film 31 and the upper peripheral wall surfaces 6a, 6b, 6c, 6d become deformable toward the inside of the container body to be curved to form an arc-shaped convex portion, thus drawn toward the center of the container together with the protection film 31, and are eventually curved. Here, each side face of the upper peripheral wall surfaces 6a, 6b, 6c, 6d is deformed in the same direction, i.e., toward the inside of the container body; however, the corners, the lower peripheral wall surfaces 7a, 7b, 7c, 7d, and the base 2 of the medical instrument housing container 1 are hardly affected by the deformation of the peripheral edges 5a, 5b, 5c, 5d and the upper peripheral wall surfaces 6a, 6b, 6c, 6d. Hence, it follows that those curved are the peripheral edges 5a, 5b, 5c, 5d and the upper peripheral wall surfaces 6a, 6b, 6c, 6d.

As a result, as shown in FIG. 4(*c*), the medical instrument housing container 1 sealed by the protection film 31 post autoclaving is in a state in which the protection film 31 covers the curved opening 4 and still seals the inside of the container body because the protection film 31 remains adhered or heat-sealed to the peripheral edge 5, the side faces of the medical instrument housing container 1 are oriented toward the inside of the container body, and the peripheral edges 5a, 5b, 5c, 5d and the upper peripheral wall surfaces 6a, 6b, 6c, 6d are deformed in an arc shape. Because the protection film 31 is less shrinkable than the peripheral edges 5a, 5b, 5c, 5d and the upper peripheral wall surfaces 6a, 6b, 6c, 6d, a flection is caused by the differential shrinkage. It should be noted that the protection film 31 in this embodiment has wrinkles 32 caused by the flection.

The medical instrument housing container 1 is used as follows.

The aseptically sealed medical instrument housing container 1 is transported to a factory where the syringe barrels 21 are to be filled with a drug, and, in the factory, the protection film 31 over the opening 4 of the medical instrument housing container 1 is removed in a clean room. Here, as shown in FIG. 2(*a*) and FIG. 4(*d*), which are plan views showing only the container body 10 of the post-sterilization medical instrument housing container 1 after removal of the protection film 31, the peripheral edge 5 to which the protection film 31 had been adhered or heat-sealed and the opening 4 of the medical instrument housing container 1 have been curved and deformed due to the deformable side faces. However, the lower peripheral wall surface 7 connecting the ledge 9 and the base 2 remains free of deformation.

To the syringe barrels 21 with the drug, for example, the medical instrument housing container 1 holding the syringe barrels 21 is placed at a predetermined position in a drug filling machine (not shown). Subsequently, using a nozzle of the drug filling machine, a predetermined dose of a desired drug is filled in the syringe barrels 21 through the proximal-end opening 26 of the respective syringe barrels 21 placed in the medical instrument housing container 1. Following this, the syringe barrels 21 locked at the upper ends of the receiving cylinders 13 in the nest member 11 are taken out of the medical instrument housing container 1 to have a plunger (not shown) inserted thereinto to make prefilled syringes. The prefilled syringes are sterilized as needed, individually enclosed in a packaging bag, and transported to medical facilities to be used by users such as doctors.

As a way of example of an embodiment of the medical instrument housing container 1 of the present invention, the shown example uses the medical instrument housing container 1 whose container body 10 initially has no deformation or curve; but its shape is changed to have a curve during sterilization by autoclaving; however, as shown in FIG. 4(*d*), a medical instrument housing container 1 molded with any pre-curved side face may be used and further curved during autoclaving.

A method of sterilization is not limited to autoclaving, but may also be ethylene oxide gas sterilization, gamma ray sterilization, or electron beam sterilization.

In sterilization that does not employ high temperature, high humidity conditions provided by high pressure steam, such as ethylene oxide gas sterilization, gamma ray sterilization, and electron beam sterilization, resin will not shrink; therefore, medical instrument housing container 1 does not undergo deformation during sterilization. In that case, the heat from the heat sealing of the protection film 31 may be used to shrink and curve the peripheral edge 5 so that the protection film 31 is flexed.

Alternatively, in sterilization where the medical instrument housing container 1 does not undergo deformation, a medical instrument housing container 1 molded with any pre-curved side face may be used, as is shown in FIG. 4(*d*). For such a medical instrument housing container 1 molded with any pre-curved side face, when adhering a protection film 31, the center of the protection film 31 can be pressured from above so that the protection film 31 is flexed.

Figure 5A:
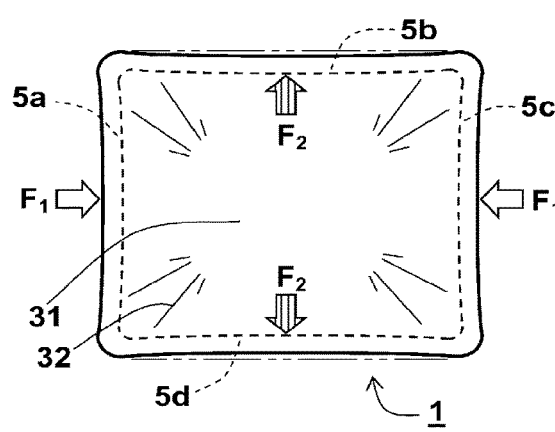
FIG. 5(a) is a schematic view showing profile change of the medical instrument housing container when a first external force is applied thereto.

Referring to FIGS. 5(*a*) to 5(*c*), profile change of the medical instrument housing container 1 when an external force is applied thereto will be described. FIGS. 5(*a*) and 5(*b*) show profile change of a medical instrument housing container 1 in accordance with an embodiment of the present invention when an external force is applied thereto. FIG. 5(*c*) shows profile change of a conventional housing container not in accordance with the present invention and having parallel opposing peripheral edges, when an external force is applied thereto.

As shown in FIG. 5(*a*), application of an external force to the medical instrument housing container 1 induces the lateral stress $F_1$ to the pair of opposing peripheral edges 5a, 5c, whereby the other pair of peripheral edges 5b, 5d therebetween is subjected to the stress $F_2$. Because the protection film 31 has been flexed, the outward stress $F_2$ is absorbed, and the flection (in this embodiment, wrinkles 32) of the protection film 31 is stretched so that deformation is buffered. Furthermore, as shown by the two-dot dashed lines, even if the peripheral edges 5b, 5d are deformed outwardly drawing the protection film 31 along therewith, the protection film 31 can follow the deformation. As a result, the protection film 31 will not be detached along the peripheral edge 5 even under the stresses $F_1$, $F_2$.

Figure 5B:
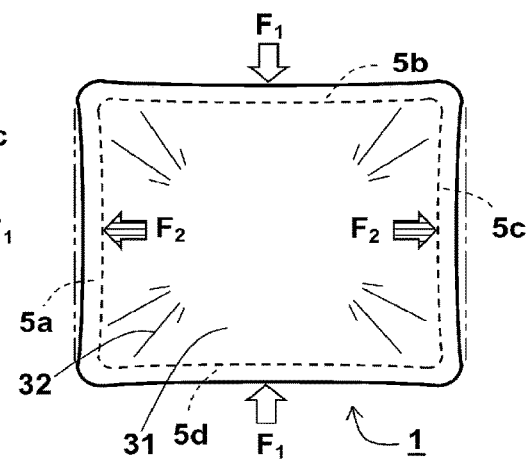
FIG. 5(b) is a schematic view showing profile change of the medical instrument housing container when a second external force is applied thereto.

Further, as shown in FIG. 5(b), application of an external force to the medical instrument housing container 1 induces the lateral stress $F_1$ to one pair of opposing peripheral edges 5b, 5d, whereby the other pair of peripheral edges 5a, 5c therebetween is subjected to the stress $F_2$. As is with the above, because the protection film 31 has been flexed, the outward stress $F_2$ is absorbed, and the flection (in this embodiment, wrinkles 32) of the protection film 31 is stretched so that deformation is buffered. Furthermore, as shown by the two-dot dashed lines, even if the peripheral edges 5a, 5c are deformed outwardly drawing the protection film 31 along therewith, the protection film 31 can follow the deformation. As a result, the protection film 31 will not be detached along the peripheral edge 5 even under the stresses $F_1$, $F_2$.

Figure 5C:
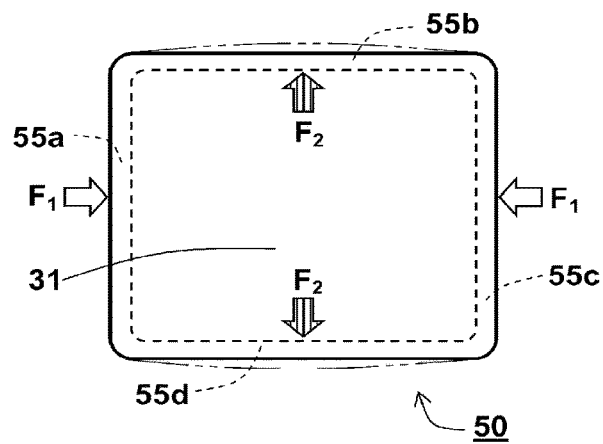
FIG. 5(c) is a schematic view showing profile change of a conventional housing container when an external force is applied thereto.

In contrast, in a conventional housing container 50 having pairs of parallel opposing peripheral edges 55a, 55c and 55b, 55d as is shown in FIG. 5(c), the protection film 31 is not flexed and, when the lateral stress $F_1$ is applied to one pair of opposing peripheral edges 55a, 55c, the other pair of opposing peripheral edges 55b, 55d is subjected to the stress $F_2$, whereby the peripheral edges 55b, 55d are outwardly deformed as is shown by the two-dot dashed lines. As a result of this outward deformation, the protection film 31 would be forcefully pulled outwardly and eventually be detached as it is unable to follow the deformation.

Especially, as is the case with the container body 10 of this embodiment, when the container body has the substantially rectangular opening 4 with a longer side of 225 to 245 mm and a shorter side of 190 to 210 mm and has the peripheral wall 3 with a thickness of 0.5 to 3 mm, the amount of outward deformation of the peripheral edge 5 caused by the stresses $F_1$, $F_2$ will be substantial, which would increase the possibility of detachment of the protection film 31. Also, as is the case with the container body 10 of this embodiment, when the peripheral wall 3 is divided by the ledge 9 into the upper peripheral wall surface 6, which is contiguous to the outer edge of the ledge 9 and extends toward the peripheral edge 5, and the lower peripheral wall surface 7, which is contiguous to the inner edge of the ledge 9 and extends toward the base 2, the stresses $F_1$, $F_2$ are concentrated to the upper peripheral wall surface 6 and the peripheral edge 5. As a result, substantial outward deformation of the peripheral edge 5 is caused, which would increase the possibility of detachment of the protection film 31.

The term "deformation" herein refers to such deformation that does not affect usage, or in other words, the medical instruments contained and the nest holding them are not affected by the deformation. In the medical instrument housing container 1 as shown in FIG. 1, which includes the peripheral edge side face 8 and the upper peripheral wall surface 6, among other deformable side faces, as deformed faces, and the lower peripheral wall surface 7 as a not deformed face, the apparent width of the ledge 9 becomes narrower after deformation. In this case, the width of the ledge 9 must be sufficient to allow mounting of the nest or nest tray. For the medical instrument housing container 1 whose side face is deformable by sterilization, a gap is provided between the upper peripheral wall surface 6 and the nest prior to use, taking possible deformation into account.

In FIGS. 1 to 3, an example of the medical instrument housing container 1 is shown with the peripheral edge 5 and its side faces, the peripheral edge side faces 8a, 8b, 8c, 8d, and the upper peripheral wall surfaces 6a, 6b, 6c, 6d all curved; however, it suffices that at least symmetrical portions in one pair of symmetric faces are deformable or deformed. For example, only one pair of opposing upper peripheral wall surfaces 6a, 6c or 6b, 6d and the contiguous peripheral edge side faces 8a, 8c or 8b, 8d of the peripheral edge 5 may be curved. Preferably the lower peripheral wall surfaces 7a, 7b, 7c, 7d of the medical instrument housing container 1 are not curved so as to maintain the strength of the medical instrument housing container 1.

When the peripheral edge side face 8a and the upper peripheral wall surface 6a are deformable, it is preferable that the peripheral edge side face 8c and the upper peripheral wall surface 6c, being their symmetric counterpart faces, are also deformable. When the lower peripheral wall surface 7a is deformable, it is preferable that the lower peripheral wall surface 7c is also deformable.

Although the medical instrument housing container 1 illustrated in FIG. 1 has the curved and deformed peripheral edge side face 8 and upper peripheral wall surface 6, if necessary, the lower peripheral wall surface 7 may be similarly curved and deformed so as to facilitate absorption of stress by the overall medical instrument housing container 1.

Any of the peripheral edge 5 and its side faces, the peripheral edge side faces 8a, 8b, 8c, 8d, the upper peripheral wall surfaces 6a, 6b, 6c, 6d, and the lower peripheral wall surfaces 7a, 7b, 7c, 7d may be curved.

The peripheral edge 5 and its side faces, the peripheral edge side faces 8a, 8b, 8c, 8d, the upper peripheral wall surfaces 6a, 6b, 6c, 6d, and the lower peripheral wall surfaces 7a, 7b, 7c, 7d may be bent, or curved while bent in the center.

The curvatures $X_1$ and $X_2$ shown in FIGS. 2(a) and 2(b) may be the same or different. When the curvatures $X_1$ and $X_2$ are the same, the width of the peripheral edge 5 to which the protection film 31 has been adhered or heat-sealed can be kept constant before and after sterilization, thus the sealed condition can be stably maintained without reducing the adhesive capacity.

The deformation in one side face alone is shown in FIG. 3. In relation to the curvatures in this side face, curvatures in deformation in an opposing or adjacent side face may be the same or different.

The materials for the body of the medical instrument housing container 1 are selected in terms of chemical resistance, heat resistance, gas and microbial barrier ability, safety for organisms, and the like. For example, polyolefin resin such as polyethylene, polypropylene, and cyclic polyolefin; polystyrene; polycarbonate; polyester such as polyethylene terephthalate; and polyamide can be used. Particularly, polypropylene is preferable for the ease of injection molding, the heat resistance against autoclaving, and the heat-sealability for the protection film 31.

To form a curve in the medical instrument housing container 1 by autoclaving, a preferable thickness of the base 2, the peripheral wall 3, the peripheral edge 5, and the ledge 9 of the medical instrument housing container 1 is from 0.5 to 3 mm. A preferable width of the peripheral edge 5 of the medical instrument housing container 1 is from 7 to 30 mm. A preferable width of the ledge 9 of the medical instrument housing container 1 is from 5 to 30 mm. Beyond these ranges, formation of a suitable curve during autoclaving will be impaired. Below these ranges, the strength will be insufficient. These ranges are also preferable for ethylene oxide gas sterilization, gamma ray sterilization, and electron beam sterilization.

The medical instrument housing container 1 is formed by molding. Usable molding can include injection molding, blow molding, compression molding, and the like.

For the protection film 31, any type of material can be used as long as it is gas permeable and impervious to particulates, including without limitation, sheets made of resin and/or paper, for example. In particular, a high-density polyethylene nonwoven sheet can be included; more particularly, TYVEK® made by DuPont is preferable. It should be noted that, "gas permeable" herein refers to steam or ethylene oxide gas permeable, while "particulates" refers to fungi, bacteria, and the like.

Thus, in accordance with the medical instrument housing container 1 whose side face(s) is deformed by curving only inwardly, outward deformation of the profile of the medical instrument housing container caused by stresses such as vibration, impacts due to fall or collision, external pressure, and the like during packing, transport, or storage thereof can be buffered, such that an associated problem of detachment of the protection film, unable to follow the profile change, can be solved.

It should be noted that, although the protection film 31 in the embodiment is flexed and has wrinkles 32, the protection film 31 may be only flexed and have no wrinkles to cover the opening 4, for example, it may cover the opening 4 being flexed toward the base 2 of the container body 10 without wrinkles.

Embodiments of the medical instrument housing container according to the present invention are useful as a container for holding medical instruments that require sterilization such as prefilled syringes and prefillable syringes therefor, syringes, needles, blood collection bags, blood collection equipment, and catheters, arranged in rows and/or hung by means of a nest therein, and for transport and storage with the sterile condition thereof maintained.

What is claimed is:

1. A medical instrument housing container comprising:
   a container body including:
      a substantially rectangular base,
      a peripheral wall having a lower end that is contiguous to a perimeter of the base and extending upward, and
      a peripheral edge portion that comprises a plurality of peripheral edges, that is contiguous to an upper end of the peripheral wall, and that extends outwardly,
   wherein the substantially rectangular base, the peripheral wall, and the peripheral edge portion are molded from resin, and the container body has an opening surrounded by the peripheral edge portion;
   one or more medical instruments held in the container body; and
   a protection film that is adhered or heat-sealed to the peripheral edge portion for covering and sealing the opening,
   wherein the medical instrument housing container is a medical instrument housing container that has been subjected to sterilization,
   wherein each of the plurality of peripheral edges of the peripheral edge portion is curved inwardly, and
   wherein the protection film comprises a plurality of outer peripheral edges, each of the plurality of outer peripheral edges of the protective film being curved inwardly along a respective one of the plurality of peripheral edges of the peripheral edge portion.

2. The medical instrument housing container according to claim 1,
   wherein the opening is substantially rectangular with a longer side having a length in a range of 225 to 245 mm and a shorter side having a length in a range of 190 to 210 mm, and
   wherein the peripheral wall has a thickness of 0.5 to 3 mm.

3. The medical instrument housing container according to claim 1,
   wherein the peripheral wall has a ledge disposed around and protruding inward from an inner wall surface of the peripheral wall, and
   wherein the medical instrument housing container further includes a nest tray configured to hold the medical instrument, the nest tray being mounted on the ledge.

4. The medical instrument housing container according to claim 3, wherein the peripheral wall is divided into an upper peripheral wall surface contiguous to an outer edge of the ledge and extending toward the peripheral edge portion and a lower peripheral wall surface contiguous to an inner edge of the ledge and extending toward the base.

5. The medical instrument housing container according to claim 3,
   wherein the one or more medical instruments comprise a plurality of syringe barrels intended to be filled with a drug, each having a cap at a distal end and a flange at a proximal end, and
   wherein a plurality of receiving cylinders configured to receive the plurality of syringe barrels is disposed such that the receiving cylinder extend through the nest tray, the receiving cylinders being organized in rows.

6. The medical instrument housing container according to claim 1, wherein at least a portion of the peripheral edge portion has an inward curvature in a range of 1 to 5 mm.

7. The medical instrument housing container according to claim 1, wherein the protection film is a nonwoven sheet made of resin that is gas permeable and impervious to particulates.

8. The medical instrument housing container according to claim 7,
   wherein the sterilization is autoclaving, and
   wherein, as a result of the autoclaving, the peripheral edge portion is curved inward and the protection film that has been adhered or heat-sealed to the peripheral edge portion is flexed.

9. The medical instrument housing container according to claim 1, wherein the peripheral edge portion has a width in a range of 7 to 30 mm.

10. The medical instrument housing container according to claim 3, wherein the ledge has a width in a range of 5 to 30 mm.

11. The medical instrument housing container according to claim 1,
    wherein the opening is substantially rectangular with a longer side having a length in a range of 225 to 245 mm and a shorter side having a length in a range of 190 to 210 mm, and
    wherein the peripheral wall has a thickness of 0.5 to 3 mm.

12. The medical instrument housing container according to claim 11,
    wherein the peripheral wall has a ledge disposed around and protruding inward from an inner wall surface of the peripheral wall, and wherein the medical instrument housing container further includes a nest tray configured to hold the medical instrument, the nest tray being mounted on the ledge.

13. The medical instrument housing container according to claim 12, wherein the peripheral wall is divided into an upper peripheral wall surface contiguous to an outer edge of the ledge and extending toward the peripheral edge portion and a lower peripheral wall surface contiguous to an inner edge of the ledge and extending toward the base.

14. The medical instrument housing container according to claim 13,
wherein the one or more medical instruments comprise a plurality of syringe barrels intended to be filled with a drug, each having a cap at a distal end and a flange at a proximal end, and
wherein a plurality of receiving cylinders configured to receive the plurality of syringe barrels is disposed such that the receiving cylinder extend through the nest tray, the receiving cylinders being organized in rows.

15. The medical instrument housing container according to claim 14, wherein at least a portion of the peripheral edge portion has an inward curvature in a range of 1 to 5 mm.

16. The medical instrument housing container according to claim 15, wherein the protection film is a nonwoven sheet made of resin that is gas permeable and impervious to particulates.

17. The medical instrument housing container according to claim 16,
wherein the sterilization is autoclaving, and
wherein, as a result of the autoclaving, the peripheral edge portion is curved inward and the protection film that has been adhered or heat-sealed to the peripheral edge portion is flexed.

18. The medical instrument housing container according to claim 17, wherein the peripheral edge portion has a width in a range of 7 to 30 mm.

\* \* \* \* \*